(12) United States Patent
Kocal

(10) Patent No.: US 8,716,522 B2
(45) Date of Patent: May 6, 2014

(54) ACETIC ACID PRODUCTION FROM BIOMASS PYROLYSIS

(75) Inventor: Joseph Anthony Kocal, Glenview, IL (US)

(73) Assignee: UOP LLC, Des Plaines, IL (US)

( * ) Notice: Subject to any disclaimer, the term of this patent is extended or adjusted under 35 U.S.C. 154(b) by 617 days.

(21) Appl. No.: 12/981,926

(22) Filed: Dec. 30, 2010

(65) Prior Publication Data

US 2012/0172622 A1     Jul. 5, 2012

(51) Int. Cl.
*C07C 51/44*     (2006.01)
*C07C 53/08*     (2006.01)

(52) U.S. Cl.
CPC .............. *C07C 51/44* (2013.01); *C07C 53/08* (2013.01)
USPC ............ 562/513; 562/515; 562/524; 562/607

(58) Field of Classification Search
CPC .......... C07C 53/08; C07C 51/42; C07C 51/44
USPC ................................................. 562/513, 607
See application file for complete search history.

(56) References Cited

U.S. PATENT DOCUMENTS

| | | |
|---|---|---|
| 3,926,947 A | 12/1975 | Lipska |
| 4,233,465 A | 11/1980 | Gallivan et al. |
| 5,264,623 A | 11/1993 | Oehr et al. |
| 6,747,067 B2 | 6/2004 | Melnichuk et al. |
| 7,670,813 B2 | 3/2010 | Foody et al. |
| 2008/0312476 A1 | 12/2008 | McCall |
| 2009/0326080 A1 | 12/2009 | Chornet et al. |
| 2010/0145097 A1 * | 6/2010 | Brtko et al. .................... 562/519 |

FOREIGN PATENT DOCUMENTS

| | | | | |
|---|---|---|---|---|
| CN | 101693845 A | * | 4/2010 | ..................... 562/519 |
| FR | 2770543 A1 | | 5/1999 | |
| WO | 2009060126 A1 | | 5/2009 | |
| WO | 2009112335 A1 | | 9/2009 | |

OTHER PUBLICATIONS

Boateng, A.A. et al.; "Pyrolysis of switchgrass (*Panicum virgatum*) harvested at several stages of maturity"; Source: Journal of Analytical and Applied Pyrolysis, v. 75, n. 2, p. 55-64, Mar. 2006.

Mahfud, F.H. et al.; "Acetic acid recovery from fast pyrolysis oil. An exploratory study on liquid-liquid reactive extraction using aliphatic tertiary amines"; Source: Separation Science and Technology, v. 43, n. 11-12, p. 3056-3074, Aug. 2008.

Kong, L. et al.; "Hydrogen production from biomass wastes by hydrothermal gasification"; Source: Energy Sources, Part A: Recovery, Utilization and Environmental Effects, v. 30, n. 13, p. 1166-1178, Aug. 2008.

Bimbela, F. et al.; "Hydrogen production by catalytic steam reforming of acetic acid, a model compound of biomass pyrolysis liquids"; Source: Journal of Analytical and Applied Pyrolysis, v. 79, n. 1-2 SPEC. ISS., p. 112-120, May 2007.

Gerdes, C. et al.; "Design, construction, and operation of a fast pyrolysis plant for biomass"; Source: Chemical Engineering and Technology, v. 25, n. 6, p. 167-174, Jun. 2002.

De Wild, P.J. et al.; "Biomass valorisation by staged degasification. A new pyrolysis-based thermochemical conversion option to produce value-added chemicals from lignocellulosic biomass"; Source: Journal of Analytical and Applied Pyrolysis, v. 85, n. 1-2, p. 124-133, May 2009.

* cited by examiner

*Primary Examiner* — Yong Chu
(74) *Attorney, Agent, or Firm* — Maryann Maas

(57) ABSTRACT

Methods are disclosed for producing, from renewable carbon sources, acetic acid in an economical manner. In particular, these methods are directed to the separation and recovery of acetic acid as a substantial product (e.g., as much as 5% by weight or more) of biomass pyrolysis. For a given commercial biomass pyrolysis unit, the acetic acid yield can represent a significant quantity of that used in a major industrial applications such as purified terephthalic acid (PTA) production. According to some embodiments, pyrolysis conditions and/or flow schemes advantageously improve the recovery of acetic acid for a given purity level.

17 Claims, 1 Drawing Sheet

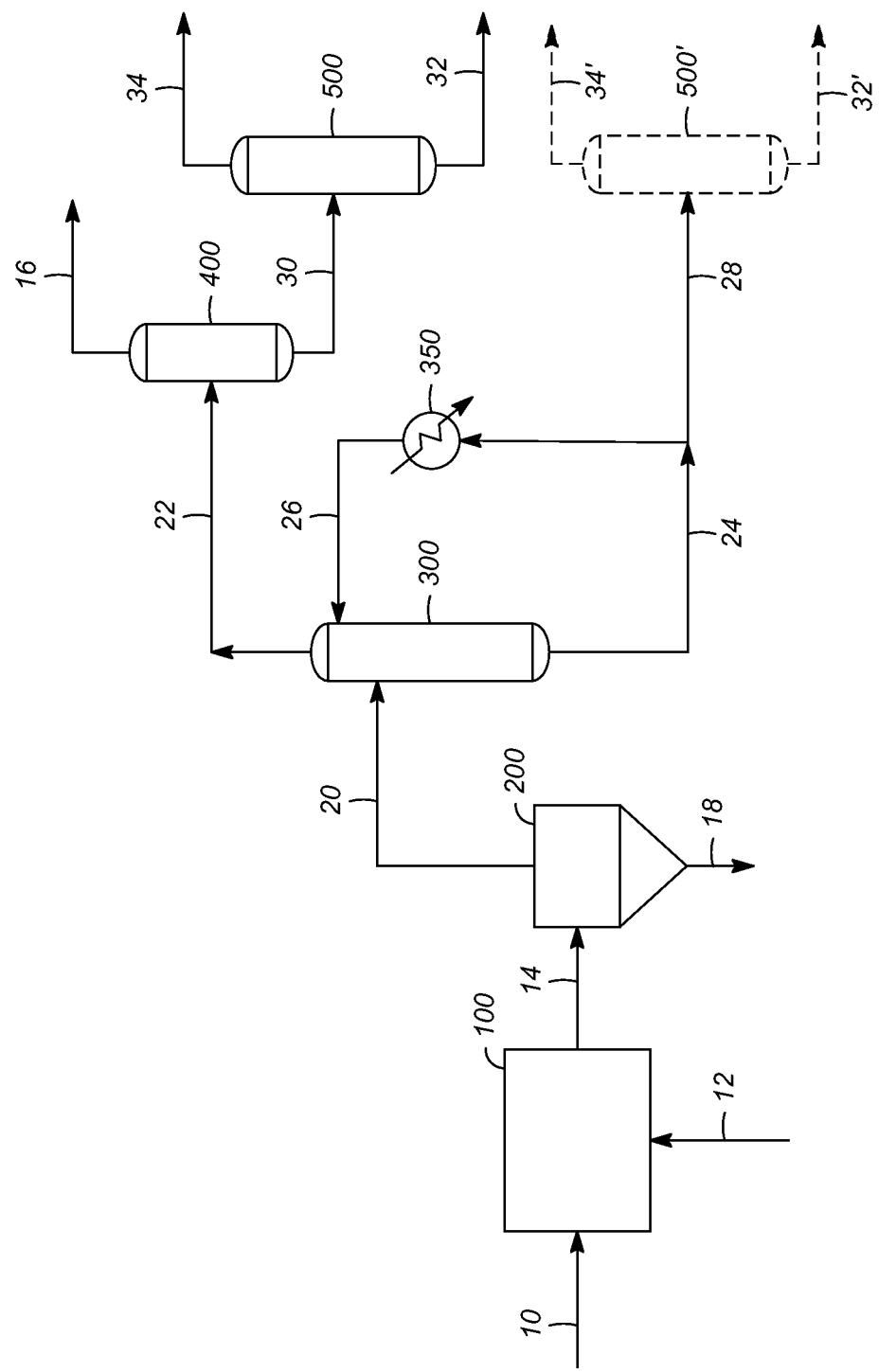

ACETIC ACID PRODUCTION FROM BIOMASS PYROLYSIS

FIELD OF THE INVENTION

The present invention relates to methods comprising pyrolyzing biomass (e.g., a lignocellulosic material) and recovering acetic acid, for example at a purity level of at least about 95% by weight, from the pyrolysis reactor effluent. Conditions for the separation of this effluent, for example prior to downstream hydroprocessing of a major portion of this effluent, may be selected to facilitate acetic acid purification and/or enhance recovery.

DESCRIPTION OF RELATED ART

Acetic acid is a high volume chemical that is utilized as a reactant, solvent, or catalyst in numerous processes. For example, acetic acid is converted according to known reaction pathways to vinyl acetate monomer (VAM), which is polymerized to form latex emulsion resins for paints and adhesives. Also, fibers and plastics are manufactured from acetic anhydride, which is another conversion product of acetic acid. An important industrial use for acetic acid as a solvent is in the production of purified terephthalic acid (PTA) by the oxidation of para-xylene with air in solution. PTA is used principally as a precursor of polyethylene terephthalate (PET) for clothing and plastic bottle manufacture, as well as other high-performance multi-purpose plastics such as polybutylene terephthalate (PBT) and polytrimethylene terephthalate (PTT). Global consumption of PTA is projected to exceed 50.5 million metric tons by the end of the year 2012, based on a report by Global Industry Analysts, Inc.

In the case of PTA production, some of the acetic acid solvent is oxidized to $CO_2$ as an unwanted byproduct. This contributes not only to the overall consumption that must be replaced through the addition of make-up acetic acid, but also to the greenhouse gas (GHG) emissions associated with the PTA production process. In view of its relatively high cost, an alternative source of less expensive acetic acid would be highly desirable. Additionally, a source of acetic acid based on renewable rather than sequestered (e.g., fossil fuel) carbon would reduce the carbon footprint of PTA production, in addition to numerous other processes utilizing the acetic acid for various end uses. Currently, the most prevalent route to acetic acid manufacture is based on the carbonylation of methanol, which is most often derived from the methane of a fossil fuel, namely natural gas.

Environmental concerns over emissions of such fossil-derived carbon in GHGs have led to an increasing emphasis on renewable energy sources. Wood and other forms of biomass including agricultural and forestry residues are examples of renewable feedstocks, which are currently being considered as a basis for the production of liquid fuels. Energy from biomass based on energy crops such as short rotation forestry, for example, can contribute significantly towards the objectives of the Kyoto Agreement in reducing greenhouse gas (GHG) emissions.

Pyrolysis is considered a promising route for achieving this objective of converting biomass feedstocks to liquid fuels, including transportation fuel and heating oil. Pyrolysis refers to thermal decomposition in the substantial absence of oxygen (or in the presence of significantly less oxygen than required for complete combustion). Initial attempts to obtain useful oils from biomass pyrolysis yielded predominantly an equilibrium product slate (i.e., the products of "slow pyrolysis"). In addition to the desired liquid product, roughly equal proportions of non-reactive solids (char and ash) and non-condensible gases were obtained as unwanted byproducts. More recently, however, significantly improved yields of primary, non-equilibrium liquids and gases (including valuable chemicals, chemical intermediates, petrochemicals, and fuels) have been obtained from carbonaceous feedstocks through fast (rapid or flash) pyrolysis at the expense of undesirable, slow pyrolysis products.

Fast pyrolysis refers generally to technologies involving rapid heat transfer to the biomass feedstock, which is maintained at a relatively high temperature for a very short time. The temperature of the primary pyrolysis products is then rapidly reduced before chemical equilibrium is achieved. The fast cooling therefore prevents the valuable reaction intermediates, formed by depolymerization and fragmentation of the biomass building blocks, namely cellulose, hemicellulose, and lignin, from degrading to non-reactive, low-value final products. A number of fast pyrolysis processes are described in U.S. Pat. No. 5,961,786; Canadian Patent Application 536,549; and by Bridgwater, A. V., "Biomass Fast Pyrolysis," Review paper BIBLID: 0354-9836, 8 (2004), 2, 21-49. Fast pyrolysis processes include Rapid Thermal Processing (RTP), in which an inert or catalytic solid particulate is used to carry and transfer heat to the feedstock. RTP has been commercialized and operated with very favorable yields (55-80% by weight, depending on the biomass feedstock) of raw pyrolysis oil.

The raw pyrolysis oil typically contains a relatively high oxygen content and relatively low energy content, compared to petroleum derived liquid fuel components. Other properties of this oil (e.g., high acidity and viscosity) render it generally unusable, in any appreciable proportion, as a component of a transportation fuel composition. Significant upgrading, however, may be achieved by hydroprocessing of the raw pyrolysis oil. Despite recent progress in the area of biofuel development, however, there remains a need in the art for the production of chemicals such as acetic acid from renewable resources, in a manner that achieves high purity and recovery of the desired compound. The fossil-derived GHG emissions associated with number of end products, including polymers, can be significantly reduced if renewable carbon is used in the generation of the associated chemical solvents and reactants consumed in their manufacturing processes.

SUMMARY OF THE INVENTION

Aspects of the present invention are associated with the discovery of methods for producing, from renewable carbon sources, acetic acid in a manner that is generally less expensive than conventional routes (e.g., methanol carbonylation) based on fossil-derived carbon sources. These methods address the separation and recovery of acetic acid as a substantial product of biomass pyrolysis. In particular, as much as 5% by weight or more of the pyrolysis product (or pyrolysis reactor effluent) can be acetic acid, depending on the biomass feedstock and pyrolysis conditions. For a given commercial biomass pyrolysis unit, this yield can represent a significant quantity, for use in a commercial chemical application such as purified terephthalic acid (PTA) production. According to some embodiments, pyrolysis conditions and/or flow schemes advantageously improve the recovery of acetic acid for a given purity level.

Representative pyrolysis processes adapted for acetic acid production have at least two stages for separation/condensation of the pyrolysis reactor effluent. A first separation stage condenses an aqueous phase comprising, in addition to water, acetic acid as well as other oxygen-containing compounds (oxygenates) having higher and lower boiling points relative to acetic acid. These include cellobiose and relatively smaller amounts of formic acid, acetaldehyde, formaldehyde, acetone, hydroxyacetone, furfural, and trace amounts of oxygenates having a higher boiling point than furfural. According to various embodiments of the invention, operating conditions of the first stage are adjusted to increase the proportion of acetic acid, present in the pyrolysis reactor effluent, in either the condensed aqueous phase or the overhead vapor exiting the first stage. In case of vaporized acetic acid exiting the first separation stage, this may be purified from the overhead vapor by distillation, for example after first removing, in a second separation stage, light components by flash separation. According to some embodiments, this flash separation may be used to obtain a second stage bottoms product enriched in acetic acid relative to the first stage overhead product.

Depending on the quality (i.e., purity) of acetic acid required for a particular application and/or the maximum tolerable amounts of certain impurities (e.g., water), distillation may be combined with further downstream purification/separation steps including selective adsorption over a fixed or moving bed of solid adsorbent. In yet further embodiments, distillation may be combined with upstream purification/separation steps, for example membrane separation to remove water, thereby significantly decreasing the amount of material processed in the distillation column and the overall energy costs required to achieve a given combination of acetic acid purity and recovery. In general, membrane separation may be advantageous for separating the significant quantity of water present with acetic acid in the second separation stage bottoms product in acetic acid production methods described herein.

Embodiments of the invention are therefore directed to methods for producing acetic acid comprising pyrolyzing biomass (e.g., lignocellulosic material such as wood, corn stover, and/or switch grass) to provide a pyrolysis reactor effluent. The methods also comprise separating at least a portion of the pyrolysis reactor effluent in a first separation stage (e.g., a quenching tower that includes quench liquid recycle) to provide first stage overhead and first stage bottoms products. The methods further comprise recovering the acetic acid from the first stage overhead product or the first stage bottoms product. Recovery can involve various processing steps, some or all of which may enrich a recovered intermediate or end product (e.g., a purified acetic acid product) in acetic acid and deplete the recovered product in other compounds (e.g., water and other oxygenates) produced from pyrolysis.

Other embodiments of the invention are directed to methods for making purified terephthalic acid (PTA) comprising oxidizing para-xylene in the presence of a solvent comprising acetic acid produced according to methods described herein. Representative values for the acetic acid solvent make-up rate, to compensate for PTA production losses (e.g., due to oxidation to $CO_2$), are generally in the range from about 1% to about 6%, and typically from about 2.5% to about 4.5%, by weight relative to the PTA production rate (i.e., kg/hr of acetic acid make-up per 100 kg/hr of PTA produced).

Acetic acid as well as final products such as PTA (made using acetic acid as a reactant, solvent, or catalyst) may therefore be derived, using methods described herein, either partly or completely from renewable sources of carbon (e.g., biomass). As a result, the acetic acid and final products exhibit reduced greenhouse gas (GHG) emissions, based on a lifecycle assessment (LCA) from the time of cultivation of feedstocks (in the case of plant materials) required to produce the acetic acid, up to and including the ultimate disposal of the acetic acid or final product by the end user. As discussed above, $CO_2$ emissions resulting from the oxidation of pyrolysis-derived acetic acid (e.g., in PTA manufacturing processes) are not reported in the lifecycle GHG emission value for acetic acid or products associated with its consumption, according to U.S. government GHG emission accounting practices, as carbon derived from biomass is renewed over a very short time frame compared to carbon derived from fossil fuels (e.g., coal, natural gas, and petroleum). LCA values of emissions in terms of $CO_2$ equivalents can be calculated, for example, using SimaPro 7.1 software and Intergovernmental Panel on Climate Change (IPCC) GWP 100a methodologies.

Further embodiments of the invention are directed to purified acetic acid products derived from pyrolysis and comprising substantially pure acetic acid, meaning that the products comprise acetic acid in an amount of generally at least about 95% (e.g., from about 95% to about 99.9%) by weight, typically at least about 97% (e.g., from about 97% to about 99.7%) by weight, and often at least about 99% (e.g., from about 99% to about 99.5%) by weight.

These and other embodiments and aspects relating to the present invention are apparent from the following Detailed Description.

BRIEF DESCRIPTION OF THE DRAWING

The FIGURE depicts a representative process for the production of acetic acid from the pyrolysis of biomass, according to aspects of the invention.

The FIGURE should be understood to present an illustration of the invention and/or principles involved. In order to facilitate explanation and understanding, a simplified process flowscheme is used, in which the equipment shown is not necessary drawn to scale. Details including pumps, heaters and heat exchangers, valves, instrumentation, and other items not essential to the understanding of the invention are not shown. As is readily apparent to one of skill in the art having knowledge of the present disclosure, methods for producing acetic acid according to various other embodiments of the invention, will have configurations and components determined, in part, by their specific use.

DETAILED DESCRIPTION

The FIGURE depicts a representative method for producing acetic acid ($CH_3COOH$) having some or all of its carbon derived from renewable sources such as biomass. This method, as well as methods according to the present invention in general, involves pyrolyzing biomass. The biomass subjected to pyrolysis in an oxygen depleted environment, for example using Rapid Thermal Processing (RTP), can be any plant material, or mixture of plant materials, including a hardwood (e.g., whitewood), a softwood, or a hardwood or softwood bark. Energy crops, or otherwise agricultural residues (e.g., logging residues) or other types of plant wastes or plant-derived wastes, may also be used as plant materials. Specific exemplary plant materials include corn fiber, corn stover, and sugar cane bagasse, in addition to "on-purpose" energy crops such as switchgrass, miscanthus, and algae. Short rotation forestry products, as energy crops, include alder, ash, southern beech, birch, eucalyptus, poplar, willow, paper mulberry, Australian blackwood, sycamore, and varieties of paulownia elongate. Other examples of suitable biomass include organic waste materials, such as waste paper and construction, demolition, and municipal wastes. In general, acetic acid may be produced, according to methods described herein, by pyrolyzing any feedstock comprising lignocellulosic biomass. Because the biomass feedstocks are composed of the same building blocks, namely cellulose, hemi-cellulose, and lignin, mixtures of these various feedstocks and changing feedstock compositions, may be used generally without difficulty in the production of raw pyrolysis oils from these various feedstocks.

According to the embodiment depicted in the FIGURE, a feedstock comprising biomass 10 is introduced to pyrolysis reactor (pyrolyzer) 100 together with pyrolysis gas 12 that is shown as a single stream in the FIGURE but may, according to some embodiments, include two or more gas streams such as (i) oxygen-containing gas that partially combusts biomass 10 in pyrolysis reactor 100 and (ii) fluidizing gas that fluidizes small solid particles of biomass 10. Both the fluidizing gas and oxygen-containing gas may be obtained at least in part from the recycling of products from other unit operations in the overall process such as (i) a combustor (not shown) of char that is separated from particle-laden pyrolysis product 14 or (ii) second separation stage 400 that provides overhead product 16 containing non-condensible gases including methane, CO, $CO_2$, $H_2$, and $N_2$. Prior to entering pyrolysis reactor 100, biomass 10 normally undergoes pretreatment steps including drying and grinding to provide the moisture levels and particle sizes desired for pyrolysis, and especially using RTP.

Particle-laden pyrolysis product 14 undergoes a preliminary gas/solids separation using cyclone separator 200 to remove solid byproduct 18 comprising char and sand, the former often used as a combustion source to generate at least some of the heat required for pyrolysis. The resulting pyrolysis reactor effluent 20 is essentially free of solids and generally contains a mixture of valuable compounds obtained from depolymerization and fragmentation of cellulose, hemicellulose, and lignin. The oxygen content of pyrolysis reactor effluent 20 is generally from about 20% to about 45%, and typically from about 30% to about 35%, by weight, based on the percentage of atomic oxygen in these compounds and their overall percentages in pyrolysis reactor effluent 20. Representative compounds include organic oxygenates such as hydroxyaldehydes (e.g., hydroxyacetal), hydroxyketones (e.g., hydroxyacetone), sugars (e.g., cellobiose), carboxylic acids, phenolics, and phenolic oligomers as well as dissolved water.

Although a pourable and transportable liquid fuel, the raw pyrolysis oil that is normally recovered mainly from pyrolysis reactor effluent 20, optionally following conventional processing steps, has only about 55-60% of the energy content of crude oil-based fuel oils. Representative values of the energy content are in the range from about 19.0 MJ/liter (69,800 BTU/gal) to about 25.0 MJ/liter (91,800 BTU/gal). Moreover, this raw product is often corrosive and exhibits chemical instability. Hydroprocessing of this pyrolysis oil is therefore recognized as beneficial in terms of reducing its oxygen content and increasing its stability, thereby rendering the hydroprocessed product more suitable for blending in fuels, such as petroleum-derived gasoline. Hydroprocessing involves contacting the pyrolysis oil with hydrogen and in the presence of a suitable catalyst, generally under conditions sufficient to convert a large proportion of the organic oxygen in the raw pyrolysis oil to CO, $CO_2$, and water that are removed. After hydroprocessing, the resulting hydroprocessed pyrolysis oil has an oxygen content that is generally reduced from about 90% to about 99.9%, relative to the oxygen content of the raw pyrolysis oil.

Aspects of the present invention are associated with improving the overall value of the pyrolysis-derived product yield by recovering important compounds, and especially acetic acid, in significant quantities from biomass pyrolysis. Importantly, these compounds, often oxygenates, may be separated from the raw pyrolysis oil that is conventionally hydroprocessed, thereby preventing their conversion (i.e., deoxygenation) to lower value hydrocarbons. According to some embodiments of the invention, conditions for downstream processing of pyrolysis reactor effluent 20, for example in first and second separation stages 300, 400 (e.g., condensation stages) are selected to facilitate recovery and/or purification of the desired compound. Although the following discussion is directed to an exemplary embodiment of the invention in which acetic acid is recovered and/or purified, those skilled in the art and having knowledge of the present disclosure will appreciate that other compounds (e.g., furfural or hydroxyacetone) can likewise be separated and further purified as a desired product of biomass pyrolysis.

According to exemplary methods in which pyrolysis is integrated with hydroprocessing (not shown in the FIGURE) for the production of biofuels, generally at least about 50% by weight, typically at least about 75% by weight, and often at least about 90% by weight, of the pyrolysis reactor effluent is subjected to hydroprocessing, while minor amounts of this effluent are separated for the recovery/purification of acetic acid and/or other desired compounds. Although these methods produce hydroprocessed biofuels as a primary product, they are also within the scope of the acetic acid production methods described herein, when recovery of acetic acid is also an objective of the overall method.

According to the exemplary embodiment depicted in the FIGURE, the acetic acid production method comprises separating pyrolysis reactor effluent 20, or at least a portion thereof, in first separation stage 300 to provide first stage overhead product 22 and first stage bottoms product 24. Acetic acid may then be recovered from either or both of the first stage products 22, 24. This recovery optionally follows various further processing steps, some or all of which may enrich a recovered intermediate or end product (e.g., a purified acetic acid product) in acetic acid and deplete the recovered product in other compounds produced from pyrolysis. A representative first separation stage 300 comprises a quenching tower and includes quench liquid recycle 26, namely a portion of first stage bottoms product 24 that is recycled to the quenching tower. Heat exchanger 350 cools quench liquid recycle 26 to remove heat from first separation stage and thereby promote the net condensation of non-recycled part 28 of first stage bottoms product 24 from pyrolysis reactor effluent 20. The quenching tower of first separation stage may include multiple stages of vapor-liquid equilibrium contacting to more completely separate compounds in pyrolysis reactor effluent 20 as desired in either first stage overhead or bottoms products 22, 24, depending on their relative volatility or boiling point. Contacting efficiency may be improved using packing or trays in first separation stage 300.

Particular embodiments include recovering acetic acid from first stage overhead product 22. An exemplary method according to such embodiments includes distilling at least a portion of first stage overhead product 22 to recover the acetic acid as a purified acetic acid product that is depleted, relative to first stage overhead product 22 in one or more higher boiling oxygenates (e.g., furfural and/or hydroxyacetone) and/or one or more lower boiling oxygenates (e.g., water). For example, according to the particular embodiment depicted in the FIGURE, the step of recovering acetic acid comprises distilling a portion of first stage overhead product 22 provided after separating light components in second separation stage 400. In a specific embodiment, a flash separator may be used in second separation stage 400 to remove light components, and particularly non-condensible components and other light gases, in second stage overhead product 16. Representative light components are selected from the group consisting of ammonia, methane, ethylene, propylene, $CO$, $CO_2$, $H_2$, $N_2$, and mixtures thereof. As discussed above, some or all of these light components may be recycled to pyrolysis reactor 100 to provide at least some of the requirement for pyrolysis gas 12, such as fluidizing gas.

As illustrated in the embodiment depicted in the FIGURE, acetic acid is recovered by distilling second stage bottoms product 30, as a portion of first stage overhead product 22 that is depleted, relative to this product, in one or more lower boiling oxygenates (e.g., $CO$, $CO_2$, and water), which are preferentially removed in second stage overhead product 16. Recovery of acetic acid is therefore achieved, according to this embodiment, using acetic acid recovery column 500, which may be operated to separate oxygenates having a higher boiling point than acetic acid, such as furfural and hydroxyacetone, into acetic acid recovery column bottoms product 32 and recover acetic acid primarily in acetic acid recovery column overhead product 34 together with water. This water may be separated from acetic acid recovery column overhead product 34 in one or more further, downstream purification steps (e.g., adsorption, distillation, or membrane separation, not shown in the FIGURE) to obtain a purified acetic acid product derived from pyrolysis and comprising at least about 95% by weight acetic acid. Alternatively, due to the relatively high concentration of water generally obtained in second stage bottoms product 30, it may be advantageous to first remove water from this product, for example using membrane separation (not shown in the FIGURE), upstream of acetic acid recovery column 500, thereby significantly reducing the energy otherwise required in this column to distill water overhead.

According to alternative embodiments, depending on the composition of second stage bottoms product 30, acetic acid recovery column 500 may be operated to distill water substantially into acetic acid recovery column overhead product 34 and recover acetic acid primarily in acetic acid recovery column bottoms product 32 together with furfural, hydroxyacetone, and other oxygenates having a higher boiling point than acetic acid. Again, one or more further steps (e.g., adsorption, distillation, or membrane separation, not shown in the FIGURE) in the purification or separation of (i) acetic acid recovery column bottoms product 32, downstream of acetic acid recovery column 500 and/or (ii) second stage bottoms product 30, upstream of acetic acid recovery column 500, may be used to obtain a purified acetic acid product derived from pyrolysis and comprising acetic acid in an amount as described above.

According to yet further embodiments of the invention, acetic acid may be recovered from first stage bottoms product 24 exiting first separation stage 300. For example, with reference to the use of a first separation stage comprising a quenching tower that includes a quench liquid recycle, as discussed above, representative methods may comprise recovering the acetic acid from non-recycled part 28 of first stage bottoms product 24. Specific embodiments directed to such methods comprise distilling at least a portion of non-recycled part 28 to recover the acetic acid as a purified acetic acid product.

Recovery of acetic acid may therefore be achieved using a distillation column downstream of first separation stage 300, as discussed above, but according to these alternate embodiments acetic acid recovery column 500' (shown in phantom in the FIGURE) is used to purify non-recycled part 28 of first stage bottoms product 24, rather than second stage bottoms product 30. More specifically, distilling at least a portion of non-recycled part 28 of first stage bottoms product 24 may be used to recover the acetic acid in either (i) an acetic acid recovery column overhead product 34', as a purified acetic acid product that is depleted in one or more higher boiling oxygenates (e.g., sugars such as cellobiose) or (ii) an acetic acid recovery column bottoms product 32', as a purified acetic acid product that is depleted in one or more lower boiling oxygenates (e.g., water).

As discussed above with respect to recovery of acetic acid from first stage overhead product 22 exiting first separation stage 300, the use of acetic acid recovery column 500' to purify non-recycled part 28 of first stage bottoms product 24 may be preceded or followed by one or more further steps (e.g., adsorption, distillation, or membrane separation, not shown in the FIGURE) in the purification or separation of (i) acetic acid recovery column bottoms product 32' or acetic acid recovery column overhead product 34', downstream of acetic acid recovery column 500' and/or (ii) non-recycled part 28 of first stage bottoms product 24, upstream of acetic acid recovery column 500', in order to obtain a purified acetic acid product derived from pyrolysis and comprising acetic acid in an amount as described above.

Further aspects of the present invention relate to the operation of first separation stage 300 and/or second separation stage 400, downstream of pyrolyis reactor 100, in a manner that facilitates separation of acetic acid into, and consequently recovery of acetic acid from, either first stage overhead product 22 or first stage bottoms product 24. For example, in embodiments comprising recovering the acetic acid from the first stage overhead product 22, the step of separating at least a portion of pyrolysis reactor effluent 20 in first separation stage 300 may be carried out under first stage separation conditions (e.g., temperature, pressure, and/or recycle ratio) whereby first stage overhead product 22 comprises the majority (at least about 50%), and generally from about 50% to about 99%, of the acetic acid contained in pyrolysis reactor effluent 20 and separated in first separation stage 300. According to more specific embodiments, first separation stage 300 may be operated under separation conditions whereby first stage overhead product 22 comprises typically from about 60% to about 98%, and often from about 70% to about 97%, of the acetic acid contained in pyrolysis reactor effluent. Separation conditions of first separation stage 300 may also, or alternatively, be such that first stage overhead product 22 comprises acetic acid in an amount of generally at least about 3% (e.g., from about 3% to about 20%) by weight, typically at least about 5% (e.g., from about 5% to about 15%) by weight, and often at least about 8% (e.g., from about 8% to about 12%) by weight.

In other embodiments comprising recovering acetic acid from the first stage bottoms product 24 (e.g., from the non-recycled part 28 of the first stage bottoms product 24), the step of separating at least a portion of pyrolysis reactor effluent 20 in first separation stage 300 may be carried out under first stage separation conditions (e.g., temperature, pressure, and/or recycle ratio) whereby first stage bottoms product 24 comprises the majority (at least about 50%), and generally from about 50% to about 99%, of the acetic acid contained in pyrolysis reactor effluent 20 and separated in first separation stage 300. According to more specific embodiments, first separation stage 300 may be operated under separation conditions whereby first stage bottoms product 24 comprises typically from about 60% to about 98%, and often from about 70% to about 97%, of the acetic acid contained in pyrolysis reactor effluent. Separation conditions of first separation stage 300 may also, or alternatively, be such that first stage bottoms product 24 comprises acetic acid in an amount of generally at least about 6% (e.g., from about 6% to about 25%) by weight, typically at least about 10% (e.g., from about 10% to about 20%) by weight, and often at least about 12% (e.g., from about 12% to about 18%) by weight.

According to yet further embodiments, acetic acid may be recovered from both first stage overhead product 22 and first stage bottoms product 24 using acetic acid recovery columns 500, 500', optionally in conjunction with further steps (e.g., adsorption, distillation, or membrane separation, not shown in the FIGURE) in the purification of acetic acid from any of, any combination of, or all of, (i) acetic acid recovery column bottoms product 32, (ii) acetic acid recovery column bottoms product 32', (iii) acetic acid recovery column overhead product 34, (iv) acetic acid recovery column overhead product 34' (with steps involving products (i) through (iv) being downstream of acetic acid recovery columns 500, 500'), (v) first stage overhead product 22, and (vi) non-recycled part 28 of first stage bottoms product 24 (with steps involving products (v) and (vi) being upstream of acetic acid recovery columns 500, 500'). With respect to any particular method for recovery and purification of acetic acid from pyrolysis reactor effluent 20, according to preferred embodiments generally at least about 50% (e.g., from about 50% to about 99%), typically at least about 60% (e.g., from about 60% to about 97%), and often at least about 85% (e.g., from about 85% to about 95%) of acetic acid produced from the pyrolysis (e.g., present in pyrolysis reactor effluent 20) is recovered in one or more purified acetic acid products having a purity levels as described above (e.g., comprising at least about 95% by weight acetic acid).

Overall, aspects of the invention are directed to the recovery and purification of valuable compounds, and particularly oxygenates such as acetic acid, from pyrolysis of a renewable feedstock (e.g., biomass). The overall value of the pyrolysis product may be enhanced relative to the value obtained using conventional downstream processing techniques involving hydroprocessing of the raw pyrolysis oil, such that essentially all oxygenates are otherwise deoxygenated to hydrocarbons. Those having skill in the art, with the knowledge gained from the present disclosure, will recognize that various changes could be made in the methods described herein for producing acetic acid, without departing from the scope of the present invention. Mechanisms used to explain theoretical or observed phenomena or results, shall be interpreted as illustrative only and not limiting in any way the scope of the appended claims.

The invention claimed is:

1. A method for separating acetic acid from an acetic acid-containing biomass pyrolysis reactor effluent, the method comprising:
   (a) providing an acetic acid-containing pyrolysis reactor effluent generated by pyrolyzing biomass;
   (b) separating at least a portion of the acetic acid-containing pyrolysis reactor effluent in a first separation stage to provide first stage overhead and first stage bottoms products; and
   (c) recovering acetic acid from the first stage overhead product or the first stage bottoms product; wherein when acetic acid is recovered from the first stage overhead product, acetic acid is recovered as a purified acetic acid product that is depleted in one or more lower boiling oxygenates, and when acetic acid is recovered from the first stage bottoms product, acetic acid is recovered as a purified acetic acid product that is depleted in one or more higher boiling oxygenates.

2. The method of claim 1, wherein step (c) comprises recovering the acetic acid from the first stage overhead product.

3. The method of claim 1, wherein the first separation stage comprises a quenching tower that includes a quench liquid recycle.

4. The method of claim 2, wherein step (c) comprises distilling at least a portion of the first stage overhead product to recover the acetic acid as the purified acetic acid product.

5. The method of claim 4, wherein step (c) comprises distilling a portion of the first stage overhead product provided after separating light components in a second separation stage.

6. The method of claim 5, wherein the second separation stage comprises a flash separator.

7. The method of claim 6, wherein the light components are selected from the group consisting of ammonia, methane, ethylene, propylene, CO, $CO_2$, $H_2$, $N_2$, and mixtures thereof.

8. The method of claim 4, wherein the one or more higher boiling oxygenates comprise furfural or hydroxyacetone.

9. The method of claim 4, wherein the one or more lower boiling oxygenates comprise water.

10. The method of claim 2, wherein step (b) is carried out under first separation stage conditions whereby the first stage overhead product comprises at least about 3% by weight acetic acid.

11. The method of claim 2, wherein step (b) is carried out under first separation stage conditions whereby the first stage overhead product comprises at least about 50% of acetic acid contained in the pyrolysis reactor effluent separated in the first separation stage.

12. The method of claim 1, wherein step (c) comprises recovering the acetic acid from the first stage bottoms product.

13. The method of claim 12, wherein the first separation stage comprises a quenching tower that includes a quench liquid recycle and wherein step (c) comprises recovering the acetic acid from a non-recycled part of the first stage bottoms product.

14. The method of claim 13, step (c) comprises distilling at least a portion of the non-recycled part of the first stage bottoms product to recover the acetic acid as the purified acetic acid product.

15. The method of claim 14, wherein the one or more higher boiling oxygenates comprise cellobiose.

16. The method of claim 12, wherein step (b) is carried out under first separation stage conditions whereby the first stage bottoms product comprises at least about 6% by weight acetic acid.

17. The method of claim 12, wherein step (b) is carried out under first separation stage conditions whereby the first stage bottoms product comprises at least about 50% of acetic acid contained in the pyrolysis reactor effluent separated in the first separation stage.

* * * * *